(12) United States Patent
da Silva Curiel et al.

(10) Patent No.: US 11,992,436 B2
(45) Date of Patent: May 28, 2024

(54) METHOD AND APPARATUS FOR INSERTING AN IMPLANT IN THE CORNEA OF THE EYE

(71) Applicants: Jeannette M. A. da Silva Curiel, Camarillo, CA (US); William R. Taber, Camarillo, CA (US)

(72) Inventors: Jeannette M. A. da Silva Curiel, Camarillo, CA (US); William R. Taber, Camarillo, CA (US)

( * ) Notice: Subject to any disclaimer, the term of this patent is extended or adjusted under 35 U.S.C. 154(b) by 1017 days.

(21) Appl. No.: 16/902,946

(22) Filed: Jun. 16, 2020

(65) Prior Publication Data
US 2020/0306086 A1 Oct. 1, 2020

Related U.S. Application Data

(63) Continuation-in-part of application No. 15/558,679, filed as application No. PCT/US2016/022721 on Mar. 16, 2016, now abandoned.
(Continued)

(51) Int. Cl.
*A61F 9/007* (2006.01)
*A61F 9/00* (2006.01)
*A61F 9/013* (2006.01)

(52) U.S. Cl.
CPC .......... *A61F 9/00781* (2013.01); *A61F 9/013* (2013.01); *A61F 2009/0035* (2013.01); *A61F 2009/0043* (2013.01); *A61F 2009/0052* (2013.01); *A61F 2210/0004* (2013.01); *A61F 2250/0067* (2013.01)

(58) Field of Classification Search
CPC ........ A61B 2017/306; A61B 2017/308; A61B 2017/320052; A61F 9/0008; A61F 9/00781; A61F 9/009; A61F 9/013; A61F 2009/0035; A61F 2009/0043;
(Continued)

(56) References Cited

U.S. PATENT DOCUMENTS

| 3,308,810 | A | * | 3/1967 | Galin | ................ | A61B 5/02216 604/294 |
| 3,788,327 | A | | 1/1974 | Donowitz | | |

(Continued)

FOREIGN PATENT DOCUMENTS

CN 1285724 A 2/2001

OTHER PUBLICATIONS

International Search Report for PCT/US16/22721 dated Aug. 12, 2016.

*Primary Examiner* — Benjamin J Klein
(74) *Attorney, Agent, or Firm* — Concept IP LLP; Pejman Yedidsion

(57) ABSTRACT

Methods, devices, and systems are presented for inserting an implant in the cornea of the eye, where the implant is a microshunt; a microshunt delivery device for delivering the microshunt into the cornea may comprise the microshunt, an actuator, and a suction stabilizer; a vacuum device may be inserted in the stabilizer such that the cornea may be sucked onto a concave bottom side of the stabilizer; the microshunt may then be inserted into a hole in the suction stabilizer with the actuator; the actuator may be turned to screw the microshunt into a hole in the cornea; and the actuator may be removed from the suction stabilizer, breaking the vacuum seal and leaving the microshunt inserted in the cornea.

15 Claims, 14 Drawing Sheets

Related U.S. Application Data

(60) Provisional application No. 62/133,955, filed on Mar. 16, 2015.

(58) Field of Classification Search
CPC ...... A61F 2009/0052; A61F 2210/0004; A61F 2250/0067; A61M 35/10
See application file for complete search history.

(56) References Cited

U.S. PATENT DOCUMENTS

| | | | |
|---|---|---|---|
| 4,729,761 A | 3/1988 | White | |
| 5,009,660 A * | 4/1991 | Clapham | A61F 9/009 606/166 |
| 5,092,837 A | 3/1992 | Ritch et al. | |
| 5,300,020 A | 4/1994 | L'Esperance, Jr. | |
| 5,312,394 A * | 5/1994 | Beckman | A61F 9/013 606/171 |
| 5,411,473 A | 5/1995 | Ahmed | |
| 5,626,558 A | 5/1997 | Suson | |
| 5,626,559 A | 5/1997 | Solomon | |
| 5,702,414 A | 12/1997 | Richter et al. | |
| 5,743,868 A | 4/1998 | Brown et al. | |
| 5,807,302 A | 9/1998 | Wandel | |
| 6,007,511 A | 12/1999 | Prywes | |
| 6,045,562 A * | 4/2000 | Amano | A61F 9/013 606/166 |
| 6,203,513 B1 | 3/2001 | Yaron et al. | |
| 6,436,113 B1 * | 8/2002 | Burba | A61F 9/013 606/166 |
| 6,533,768 B1 | 3/2003 | Hill | |
| 7,879,001 B2 | 2/2011 | Haffner et al. | |
| 7,947,008 B2 | 5/2011 | Grahn et al. | |
| 8,333,742 B2 | 12/2012 | Bergheim et al. | |
| 8,444,588 B2 | 5/2013 | Yablonski | |
| 8,603,024 B2 | 12/2013 | Field et al. | |
| 8,734,378 B2 | 5/2014 | de Juan et al. | |
| 8,808,219 B2 | 8/2014 | Bergheim et al. | |
| 8,852,256 B2 | 10/2014 | Horvath et al. | |
| 11,116,625 B2 * | 9/2021 | Kalina, Jr. | A61F 2/1664 |
| 2002/0072673 A1 * | 6/2002 | Yamamoto | A61F 9/00781 600/458 |
| 2004/0147944 A1 * | 7/2004 | LaHaye | A61F 9/009 606/4 |
| 2004/0225284 A1 * | 11/2004 | Webb | A61F 9/009 606/5 |
| 2006/0173397 A1 | 8/2006 | Tu et al. | |
| 2006/0271025 A1 * | 11/2006 | Jones | A61F 9/00802 606/4 |
| 2007/0093795 A1 * | 4/2007 | Melcher | A61F 9/009 606/5 |
| 2007/0149915 A1 | 6/2007 | Yablonski | |
| 2007/0156079 A1 | 7/2007 | Brown | |
| 2007/0276316 A1 | 11/2007 | Haffner et al. | |
| 2008/0161741 A1 | 7/2008 | Bene et al. | |
| 2009/0043242 A1 | 2/2009 | Bene et al. | |
| 2009/0177138 A1 | 7/2009 | Brown et al. | |
| 2009/0187178 A1 * | 7/2009 | Muller | A61F 9/008 606/41 |
| 2012/0123317 A1 | 5/2012 | Horvath et al. | |
| 2013/0267887 A1 | 10/2013 | Kahook et al. | |
| 2014/0012177 A1 | 1/2014 | Tu et al. | |
| 2014/0243729 A1 | 8/2014 | Rynerson | |
| 2014/0276332 A1 | 9/2014 | Crimaldi et al. | |
| 2015/0011926 A1 | 1/2015 | Reitsamer et al. | |
| 2017/0266045 A1 * | 9/2017 | Kangastupa | A61M 5/46 |
| 2017/0348150 A1 * | 12/2017 | Horvath | A61F 9/00781 |
| 2018/0110650 A1 * | 4/2018 | da Silva Curiel | A61F 9/00781 |

* cited by examiner

METHOD AND APPARATUS FOR INSERTING AN IMPLANT IN THE CORNEA OF THE EYE

CROSS-REFERENCE TO RELATED APPLICATIONS

This application is a continuation-in-part of U.S. Nonprovisional patent application Ser. No. 15/558,679, filed Sep. 15, 2017, which is a U.S. National Phase Patent Application under 35 U.S.C. § 371 of International Application No. PCT/US2016/022721, filed Mar. 16, 2016, which claims the priority benefit of U.S. Provisional Patent Application No. 62/133,955, filed Mar. 16, 2015, all of which are hereby incorporated herein by reference in their entirety for all purposes.

TECHNICAL FIELD

The invention, in its several embodiments, pertains to medical devices for control of glaucoma and/or dry eye, and more particularly to a method and apparatus for inserting a glaucoma implant in the cornea of the eye.

BACKGROUND

Glaucoma is a term describing a group of eye disorders caused when the intraocular pressure within the eye increases, thereby causing retinal and optic nerve damage and subsequent loss of vision. The anterior chamber is the cavity located between the cornea and the lens, and is filled with a fluid (i.e., aqueous). Aqueous fluid is continuously produced by secretions from the ciliary body. The aqueous drains from the anterior chamber through the drainage angle and into the venous system. In a normal situation, aqueous production is equal to aqueous outflow through the drainage angle (angle), and intraocular pressure remains fairly constant in a range considered to be safe, for example, 15 to 21 mmHg range. Glaucoma occurs when aqueous does not drain sufficiently from the anterior chamber through the angle, causing an increase in intraocular pressure above the safe range. Raised intraocular pressure (generally above 21 mm Hg in humans and above 28 mm Hg in cats, dogs, and horses) is the most important and currently the only modifiable risk factor for treating glaucoma. Lowering this intraocular pressure is the major treatment goal in all glaucoma patients.

In the human eye, aqueous drains from the anterior chamber through the trabecular meshwork into a collecting channel, called Schlemm's canal. From Schlemm's canal, aqueous flows into collector channels that join Schlemm's canal, and then into the episcleral venous system. However, the anatomy of the canine, feline, and equine iridocorneal drainage angle has significant differences compared with the human eye. These eyes have pillars of tissue (pectinate ligaments) as the most anterior part of the iridocorneal angle, which communicate with a wide region (the ciliary cleft) that drains aqueous into the uveal and corneoscleral trabecular meshwork. From there, aqueous enters into one or more drainage veins that comprise the angular aqueous plexus (AAP), and then exits the eye via episcleral veins.

In all species, glaucoma can be roughly divided into two main categories, "open-angle" (or OAG) and "closed angle" or "angle-closure" (or ACG) glaucoma. In open-angle glaucoma, the anterior chamber remains open, but the exit of aqueous through the trabecular meshwork is reduced. Closed-angle glaucoma is caused by closure of the angle, preventing drainage of aqueous out of the anterior chamber.

Glaucoma can also be classified as "primary" (inherited) and "secondary" (non-inherited). Secondary glaucoma can be caused by injury, abnormal structures, inflammation, tumors, certain drugs, or diseases. Both primary and secondary glaucoma can be open or closed angle.

Despite its importance, the long-term control of human and veterinary glaucoma continues to be a challenge and is often unsuccessful in controlling the glaucoma and/or maintaining vision. Current treatments for glaucoma include medications and/or surgery to decrease intraocular fluid production, increase fluid drainage from the eye, or both.

In both human and veterinary medicine, few advancements have been made in medical and surgical therapy for glaucoma. Medical and surgical treatment is expensive and unaffordable to a large majority of human and veterinary glaucoma patients. Medications can cause side effects and are frequently ineffective in long-term control of glaucoma. When drug therapy fails, surgical therapy is needed.

Various forms of surgery to treat glaucoma include methods to open the fluid drainage channels, reduce fluid production by the ciliary body, or both. Multiple surgeries may be required, and frequently medications are also needed to help control intraocular pressure postoperatively.

In humans, there are many different surgical procedures for control of open-angle glaucoma. These surgeries involve procedures that mechanically disrupt the trabecular meshwork, improve outflow of aqueous through the drainage angle, making holes in the peripheral iris, filtering procedures (penetrating or non-penetrating), tube shunts (valved or non-valved), reduce aqueous fluid production, or involve manipulations of Schlemm's canal These surgeries are all major operations that are designed for treatment of open-angle glaucoma, Most of these surgical techniques are not applicable for the canine, feline, or equine eye because of the lack of Schlemm's canal in these species, because they are designed mainly for the treatment of open-angle glaucoma rather than closed-angle glaucoma.

Various tube-shunt drainage devices have been developed for treatment of closed-angle glaucoma and divert aqueous fluid out of the eye to the subconjunctival space (Ahmed valve, Molteno glaucoma shunt) or into the frontal sinus or nasal cavity (Cullen shunt) Shunt surgeries eventually fail due to clogging of the drainage tube, and/or due to formation of a fibrous tissue capsule over the shunt, causing decreased flow of aqueous fluid out of the eye. This causes return of glaucoma and necessitates further treatment.

All of the above surgeries have numerous disadvantages including poor long-term prognosis for control of glaucoma. They need to be performed in an operating room, involve substantial trauma to the eye, require great surgical skill, have the potential for significant complications, are expensive, and have limited to no availability for many pet owners. Most significantly, the anatomy of the canine, feline, and equine iridocorneal filtration angle has significant differences compared with the human eye, which renders most human glaucoma-management surgeries ineffective in dogs, cats, and/or horses Acute angle-closure glaucoma in dogs is an emergency and requires that the intraocular pressure be reduced to a safe range within minutes or hours. Glaucoma surgeries which attempt to preserve vision are often declined by clients because they may need to travel long distances to find a veterinary ophthalmologist that can provide such surgeries, the cost of surgery is very expensive, pre- and post-surgical treatments are time-consuming and expensive, and the patient may be uncooperative. If treatment is delayed, permanent blindness will usually occur, often within a matter of a few hours. In most dogs, glaucoma is also a very painful condition. Once the eye is blinded by glaucoma, then glaucoma-eliminating surgery (such as enucleation, i.e., removal, of the eye, evisceration of the eye with surgical placement of an intraocular prosthesis, or an ablation procedure) is required to restore comfort and eliminate the requirement for treatment. Therefore, new surgical approaches need to be developed that provide faster, better, safer, and less expensive care for both human and veterinary glaucoma patients, both in the short- and long-term.

SUMMARY

A device embodiment of the microshunt device may comprise: an inlet section comprising at least one lumen and at least one inlet opening; an outlet section comprising at least one lumen that connects to at least one outlet opening; and wherein the microshunt device is configured to be implanted within a cornea of an eye, wherein the microshunt device effects the flow of aqueous humor from an anterior chamber of the eye to the anterior surface of the cornea, bypassing the trabecular meshwork, thereby diverting aqueous humor from the anterior chamber to the surface of the cornea; and wherein the microshunt is prevented from migrating from an implantation site. The microshunt device may further comprise a plurality of lumens arranged in a series and parallel to each other. Optionally, the microshunt device may be retained, before implantation, via a plunger-type deployment mechanism. Additionally, the microshunt device may be deployed from an applicator and once a distal section of the applicator passes beyond a corneal endothelium and into the anterior chamber.

In another embodiment, the microshunt deployment may be facilitated by the plunger-type deployment mechanism with an associated deployment actuator mounted on a handle of the applicator. Optionally, the microshunt device may utilize fluid flow from a higher pressure environment to a lower pressure environment. In one embodiment, the microshunt device may further comprise a flow-restricting member within the lumen that may be configured to: control globe decompression after the microshunt is implanted; and control flow of the aqueous humor out of the eye. Additionally, the flow-restricting member within the lumen may act to partially fill the lumen; and the flow-restricting member within the lumen may be a wire having a diameter thickness smaller than the lumen. In some embodiments, the flow-restricting member may be further configured to control the flow of aqueous humor based on thickness of diameter.

A system embodiment may comprise: a barrel holder, wherein the holder may have a proximal end and a distal end, wherein the proximal end of the holder contains a plunger and the distal end contains an extrusion tip; wherein the extrusion tip further comprises a first lumen and at least one irrigating hole disposed between the proximal and distal ends of the extrusion tip; wherein the irrigating hole is in fluid communication with the lumen; a microshunt device, wherein the microshunt device is configured to be implanted within a cornea of an eye, and wherein the microshunt effects the flow of aqueous humor from an anterior chamber of the eye to the anterior surface of the cornea, bypassing the trabecular meshwork; and a barrel holder comprising a second lumen, wherein a distal end of the second lumen opens to the distal end of the extrusion tip portion; and wherein the holder is configured to hold the microshunt device during implantation of the microshunt device within the eye, and the holder releases the microshunt device upon deployment of the microshunt device. Optionally, the proximal end of the second lumen may be separated from the first lumen of the extrusion tip. Additionally, fluid may be infused through a lumen of the microshunt into the anterior chamber. In one system embodiment, the system may further comprise a flow-restricting member configured to: control globe decompression after the microshunt is implanted; and control flow of aqueous out of the eye.

A method embodiment may comprise the steps of: providing a microshunt for diverting aqueous humor from the anterior chamber of a cornea to the surface of the cornea; providing an applicator for delivering the microshunt into the cornea; creating an incision in and through the cornea for the microshunt placement via a distal portion of the applicator comprising a cutting tool; placing tightly, the microshunt within the cannula lumen of the applicator, wherein the microshunt is retained by a plunger-type deployment mechanism; deploying the microshunt, from the applicator, once the distal section passes beyond the corneal endothelium and into the anterior chamber; and regulating the flow of the aqueous humor via the deployed microshunt once implanted, thereby the aqueous humor flows controllably from an anterior chamber of the eye to the anterior surface of the cornea, bypassing the trabecular meshwork. Optionally, securing the microshunt may be via a fastening mechanism.

The regulating of the flow of the aqueous humor via the deployed microshunt may further comprise employing a flow-restricting member. In one embodiment, the regulating of the flow of the aqueous humor via the deployed microshunt may further comprise: controlling globe decompression after the microshunt is deployed and implanted via the flow-restricting member. Additionally, the flow-restricting member may be a wire having a diameter thickness that is less than diameter thickness of the microshunt.

BRIEF DESCRIPTION OF DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which.

DETAILED DESCRIPTION

Figure 1:
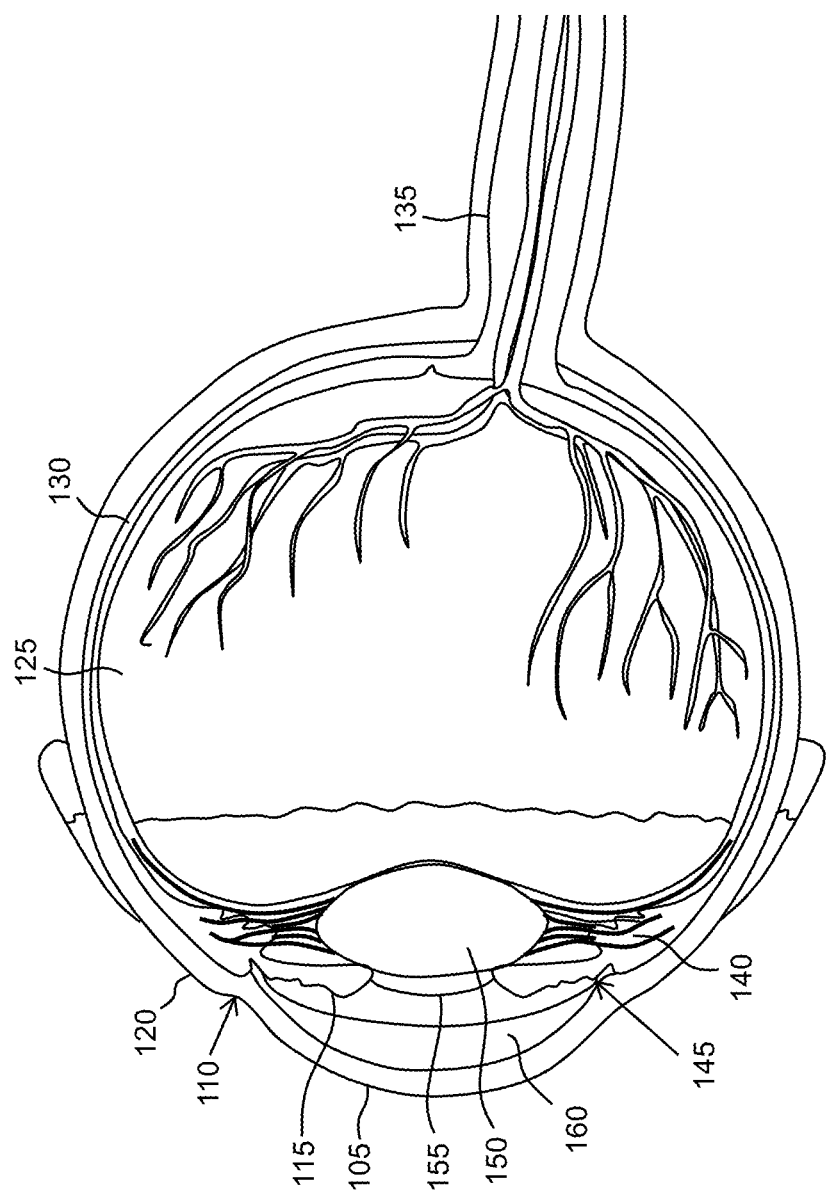
FIG. 1 is a cross-sectional view of a mammalian eye.

To overcome the difficulties outlined above, the present application discloses a microshunt device and method of treatment for glaucoma that diverts aqueous humor from the anterior chamber to the surface of the cornea. The exterior surface of the cornea is a readily-accessible site for long-term extraocular diversion of aqueous fluid from within the eye for the purpose of controlling glaucoma. Additionally, the present application provides for a microshunt to be implanted into the cornea so that aqueous fluid may be drained from the anterior chamber to the surface of the cornea, via the microshunt, such that the microshunt is prevented from migrating from its implantation site, for example, with a silver anti-microbial core, and an optional temporary flow-restricting member designed to (a) control globe decompression after the microshunt is implanted; (b) control flow of aqueous out of the eye; and (c) in the event of microshunt plugging, may be used to restore microshunt patency.

Some embodiments of the apparatus for inserting a glaucoma implant in the cornea of the eye may include devices and methods for treatment of intraocular pressure due to glaucoma. A hollow microshunt may be adapted for implantation within the cornea of an eye such that aqueous humor flows controllably from an anterior chamber of the eye to the anterior surface of the cornea, bypassing the trabecular meshwork. In one embodiment, the microshunt may comprise a quantity of antimicrobial pharmaceuticals to reduce the possibility of corneal and/or intraocular infection.

A corneal implant device, and the method and apparatus for inserting the microshunt implant into the cornea of the eye is disclosed herein. The corneal implant may include a small hole, cavity, orifice, or group of orifices that allow leakage of fluid from the eye onto the surface of the cornea. The rate of leakage of fluid from the eye may be intended, by design of the implant, to match the normal production of fluid by the eye such that pressure buildup associated with glaucoma is controlled to an acceptable pressure level. One embodiment of the corneal implant may comprise a wire or partial plug element that is coaxially located within the implant device. The wire or plug element may be one of many possible materials including silver metal. Another embodiment of the corneal implant may allow the adjustment of leakage rate by removing the coaxial element and substitution of either a smaller or larger element; where the diameter of the element may affect the size of the orifice and thereby the fluid flow. The implant may also be designed to allow fluids of all types to be injected through the corneal implant into the interior of the eye. Accordingly, the implant may facilitate the flow of fluid on both directions, i.e., in and out of the eye.

One embodiment of the apparatus for inserting a glaucoma implant in the cornea of the eye provides a microshunt that is implantable within a cornea. The microshunt may comprise an inlet section comprising at least one lumen and one inlet opening, an outlet section having at least one lumen that connects to at least one outlet opening, where the lumen is an inside space of a tubular structure. In one embodiment, the microshunt may further comprise a flow-restricting member within the lumen that is configured to permit fluid entering the lumen of the inlet section to pass through the flow-restricting member, enter the lumen of the middle section, pass into the lumen of the outlet section, and then exit the outlet section.

Other embodiments of the apparatus for inserting a glaucoma implant in the cornea of the eye, may provide an apparatus for implanting a microshunt within a cornea such that the implant is placed through the cornea to drain aqueous from the anterior chamber to the surface of the cornea. The apparatus may comprise a syringe portion and a cannula portion that has proximal and distal ends. The proximal end of the cannula portion is attached to the syringe portion. The cannula portion further comprises a first lumen and at least one irrigating hole disposed between the proximal and distal ends of the cannula portion. The irrigating hole is in fluid communication with the lumen. The apparatus further includes a holder including a second lumen for holding the microshunt. A distal end of the second lumen opens to the distal end of the cannula portion, and a proximal end of the second lumen may be separated from the first lumen of the cannula portion. The holder may function to hold the microshunt during implantation of the device within the eye, and the holder releases the microshunt when a practitioner activates deployment of the device. In some embodiments, fluid is infused through a lumen of the microshunt into the anterior chamber In one embodiment, the apparatus for inserting a glaucoma implant in the cornea of the eye may be arranged where the fluid is at least one of a salt solution or viscoelastic.

Optionally, the fluid may comprise a therapeutic substance such as a pharmaceutical, a gene, a growth factor, and/or an enzyme. In other embodiments, the fluid may comprise a therapeutic substance such as an antiglaucoma drug, a beta-adrenergic antagonist, a TGF-beta compound, and/or an antibiotic. In yet other embodiments, the infusing lumen of the microshunt device may further comprise coupling the inflow portion of the microshunt with a fluid delivery element that transmits the fluid to the microshunt. Optionally, the apparatus for inserting a glaucoma implant in the cornea of the eye may be so that the coupling comprises securing a screw thread arrangement of the fluid delivery element with a receiving thread arrangement of the microshunt.

The present application may generally relate to medical devices and method for continuously decompressing elevated intraocular pressure in eyes affected by glaucoma and/or for treatment of dry eye by diverting aqueous humor from the anterior chamber of the animal eye onto the surface of the cornea through a surgically implanted shunt. The shunt devices may provide uni-directional or bi-directional flow of fluid through the cornea. The shunt may include a silver-lined hollow tube and/or a silver-impregnated antimicrobial material, having a length sufficient to span the distance between the corneal endothelial surface and the outside of the cornea, and a seal device to anchor the shunt device within the cornea. In some embodiments, the shunt may also include a fluid pressure openable valve or a sphincter valve in the tube, allowing for controlled flow of aqueous humor from the anterior chamber through the tube on to the corneal surface when implanted.

In one embodiment, the apparatus may include a handpiece device to implant the microshunt; where the handpiece may have a distal end and a proximal end; a (sharp) tip connected to the distal end of the handpiece, the sharp tip having a distal portion and being configured to perform a corneal incision and into the anterior chamber of the eye; a holder attached to the distal portion of the elongate tip, the holder configured to hold and release the microshunt; and an actuator on the handpiece that actuates the holder to release the microshunt from the holder into the cornea.

Embodiments of the present application further describe surgical and therapeutic treatment of glaucoma through reduction of intraocular pressure via the use of the microshunt. While the description sets forth various embodiment specific details, the description is illustrative only and should not be construed in any way as limiting the invention. Furthermore, various applications of the invention, and modifications thereto, which may occur to those who are skilled in the art, are also encompassed by the general concepts described below.

Figure 2:
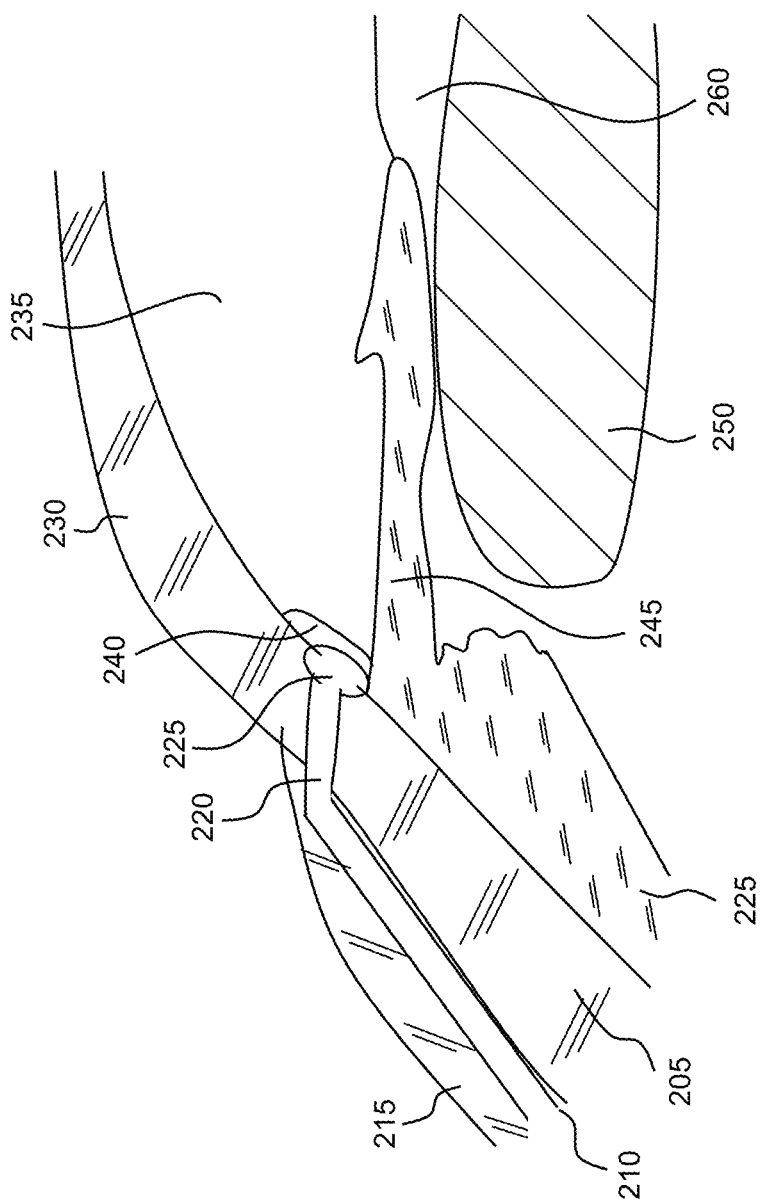
FIG. 2 is a close-up view showing the relative anatomical locations of the trabecular meshwork, the anterior chamber, and the cornea.

FIG. 1 is a cross-sectional view of a mammalian eye, while FIG. 2 is a close-up view showing the relative anatomical locations of the trabecular meshwork (145), the anterior chamber (160), and the cornea (105). The sclera (120) is a thick collagenous tissue that covers the entire eye except a portion that is covered by the cornea (105). The cornea (105) is a thin transparent tissue that focuses and transmits light into the eye and through the pupil (155), which is a circular hole in the center of the iris (115) (colored portion of the eye). The cornea (105) merges into the sclera (120) at a juncture referred to as the limbus (110). The ciliary body (140) extends along the interior of the sclera and is coextensive with the choroid (130). The choroid (130) is a vascular layer of the eye, located between the sclera (120) and the retina (125). The optic nerve (135) transmits visual information to the brain and is the anatomic structure that is progressively damaged by glaucoma.

Figure 3:
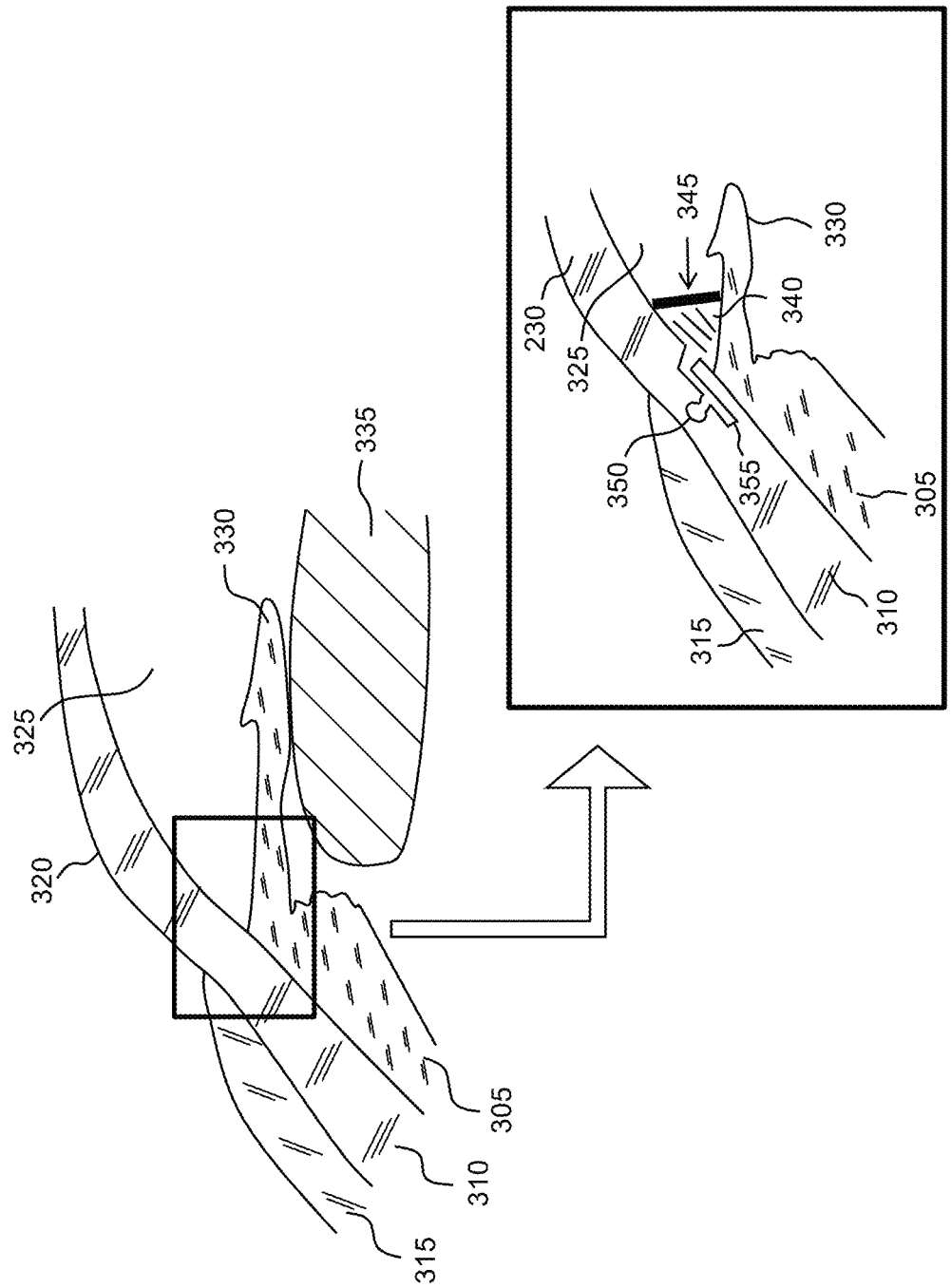
FIG. 3 is a cross-sectional view of the non-primate mammalian drainage angle.

FIG. 2 is a cross-sectional view of a primate drainage angle; as shown in FIGS. 2 and 3, the anatomy of the drainage angle of the primate eye (FIG. 2) is considerably different from the anatomy of the drainage angle of the non-primate mammalian eye (FIG. 3). The anterior chamber (235) of the eye, which is bound anteriorly by the cornea (230) and posteriorly by the iris (245) and the lens (250), is filled with aqueous humor (hereinafter referred to as "aqueous"). Aqueous is produced by the ciliary body (255), then moves anteriorly through the pupil (260) and reaches the anterior chamber angle, formed between the iris and the cornea. In a normal eye, aqueous is removed from the anterior chamber through the trabecular meshwork (240). Aqueous passes through the trabecular meshwork into Schlemm's canal (225) and thereafter through a plurality of aqueous collector veins (220), which merge with episcleral blood-carrying veins (210), and into systemic venous circulation. Intraocular pressure is maintained by an intricate balance between secretion and outflow of aqueous in the manner described above. Glaucoma is, in most cases and as described previously, characterized by an excessive buildup of aqueous in the anterior chamber, which leads to an increase in intraocular pressure. Fluids are relatively incompressible, and thus intraocular pressure is distributed uniformly throughout the eye.

Traditional procedures that create a hole or opening for implanting a device through the tissues of the conjunctiva (215) and sclera (205), or inserting a microshunt through trabecular meshwork (240) having a distal portion disposed within Schlemm's canal (225) and a proximal portion disposed within the anterior chamber of the eye (235), involve extensive surgery, as compared to surgery for implanting a device, as described herein, which ultimately resides entirely within the confines of the cornea (230).

FIG. 3 is a cross-sectional view of the non-primate mammalian drainage angle. The anterior chamber (325) of the eye, which is bound anteriorly by the cornea (320) and posteriorly by the iris (330) and the lens (335), is filled with aqueous humor (hereinafter referred to as "aqueous"). Aqueous is produced by the ciliary body (305), then moves anteriorly through the pupil (360) and reaches the anterior chamber angle, formed between the iris and the cornea. Aqueous drains between pillars of tissue (pectinate ligaments) (345) as the most anterior part of the iridocorneal angle, which communicate with a wide region (the ciliary cleft) (340) that drains aqueous into the uveal and corneoscleral trabecular meshwork. From there, aqueous enters into one or more drainage veins that comprise the angular aqueous plexus (AAP) (355), and then exits the eye via the intrascleral venous plexus (350) which drain into episcleral veins between the sclera (310) and the conjunctiva (315). Note the absence of a Schlemm's canal in the non-primate mammalian drainage angle.

Figure 4C:
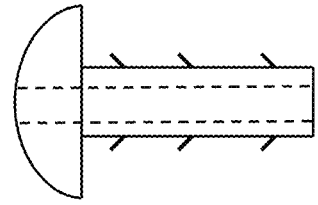
FIGS. 4A-F show a detailed external view of various embodiments of a microshunt.
Figure 4F:
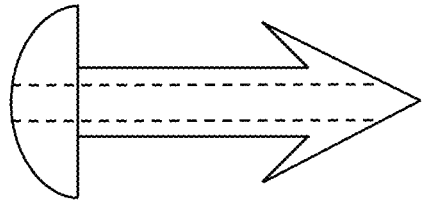
Figure 4B:
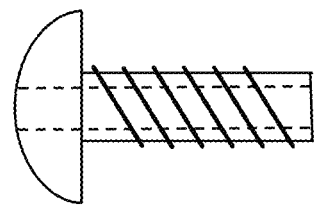
Figure 4E:
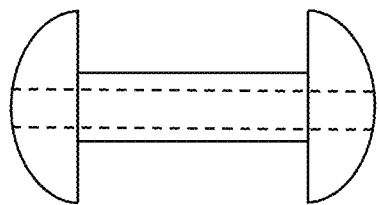
Figure 4A:
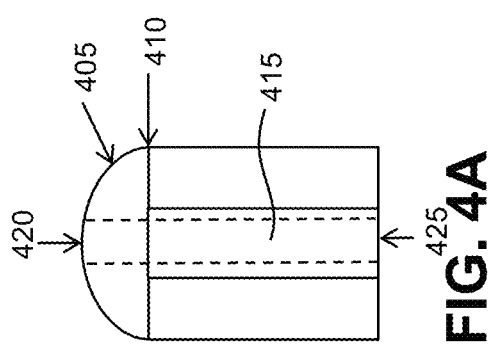
Figure 4D:
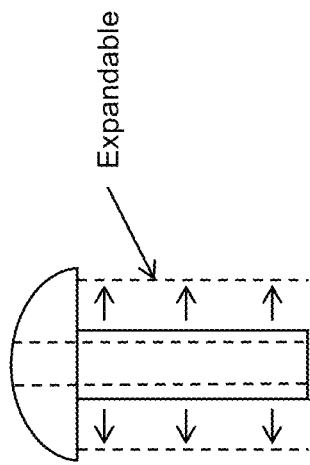

FIG. 4A depicts an embodiment of a hollow microshunt (405) that may be used in order to facilitate/effect the outflow of aqueous from the anterior chamber through the cornea onto the surface of the cornea (410), and so that the intraocular pressure is reduced. In a cross-section of the illustrated embodiment, the microshunt comprises an inlet section, having an inlet opening (425), a middle section (415), and an outlet section (420) having at least one opening. The middle section (415) may be an extension of, or may be coextensive with, the inlet section. The device comprises at least one lumen within section, which is in fluid communication with the inlet opening and the outlet opening thereby facilitating transfer of aqueous through the device.

The lumen and the remaining body of the outlet section may have a cross-sectional shape that is oval, circular, or other appropriate shape. In one embodiment, the middle section may have a length that is roughly slightly larger than the thickness of the cornea, which typically ranges between about 400 μm and about 800 μm.

To further stent, shunt, or open the outflow pathway after implanting the microshunt, a plurality of elevated, that is, protruding axially, supports or pillars may be located at the distal-most end of the outlet section sized and configured for allowing media, for example, aqueous, liquid, balanced salt solution, viscoelastic fluid, therapeutic agents, or the like, to be transported freely.

The microshunt may further comprise a flow-restricting member, which is tightly retained within a lumen. The flow-restricting member is sized and configured for maintaining a safe (normal) intraocular pressure of the fluid within the anterior chamber for a suitable period of time. Alternatively, the flow-restricting member may be situated in any location within the device such that fluid flow is restricted such that intraocular pressure is maintained at a safe level within the anterior chamber. The flow-restricting member may, in other embodiments, be a filter made of a material selected from, but not limited to, the following filter materials: expanded polytetrafluoroethylene, cellulose, ceramic, glass, Nylon, plastic, and fluorinated material such as polyvinylidene fluoride ("PVDF").

The microshunt allows leakage from the higher pressure environment, i.e., eye interior, to the lower pressure environment, i.e., eye exterior. The microshunt device may incorporate a small orifice or series of orifices arranged either in series or parallel or a combination thereof. The calculated effective orifice size may have a 0.001 inch diameter. An exemplary method to control the fluid flow may be one in which a small effective diameter hole may be created by partially filling an initial hole or orifice with a plug element. The plug element may, for example, comprise a fine diameter wire where the diameter of the wire is less than the diameter of the initial hole or orifice. A plug may also allow the microshunt performance to be fine-tuned prior to surgical implantation or allow a microshunt assembly to be tuned after surgery. In one embodiment, the effective orifice may even be a fused filter material. Optionally, a tool may be designed that may hold the microshunt body and allow a plug element to be removed and replaced with a different plug element having a different diameter, for example, that might be smaller or larger than the original plug.

The microshunt may be made by, for example, molding, thermo-forming, sintering, or other micro-machining techniques. The microshunt may comprise a biocompatible material such that inflammation arising due to irritation between the outer surface of the device and the surrounding tissue is minimized. Biocompatible materials which may be used for the device may include, but are not limited to, titanium, stainless steel, medical grade silicone, e.g., Silastic™, available from Dow Corning Corporation of Midland, Mich.; and polyurethane, e.g., Pellethane™, also available from Dow Corning Corporation. In other embodiments, the device may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicone, and/or a mixture of the aforementioned biocompatible materials, and the like. In another embodiment, the microshunt may be made of a biodegradable material selected from a group consisting of poly (lactic acid), polyethylene-vinyl acetate, poly (lactic-co-glycolic acid), poly (D,L-lactide), poly (D,L-lactide-co-trimethylene carbonate), poly (caprolactone), poly (glycolic acid), and copolymer thereof. In other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists, TGF-beta, and other anti-glaucoma drugs, or antibiotics), and similar material.

As is well known in the art, a device coated or loaded with a slow-release substance may have prolonged effects on local tissue surrounding the device. The slow-release delivery may be designed such that an effective amount of substance is released over a desired duration. "Substance," as used herein, is defined as any therapeutic or active drug that may stop, mitigate, slow-down or reverse undesired disease processes.

In one embodiment, the device may be made of a biodegradable—also including bio-erodible—material admixed with a substance for substance slow-release into ocular tissues. In another embodiment, polymer films may function as substance containing release devices whereby the polymer films may be coupled or secured to the device. The polymer films may be designed to permit the controlled release of the substance at a chosen rate and for a selected duration, which may also be episodic or periodic. Such polymer films may be synthesized such that the substance is bound to the surface or resides within a pore in the film so that the substance is relatively protected from enzymatic attack. The polymer films may also be modified to alter their hydrophilicity, hydrophobicity and vulnerability to platelet adhesion and enzymatic attack. The device may be used for a direct release of pharmaceutical preparations into ocular tissues. As discussed above, the pharmaceuticals may be compounded within the device or form a coating on the device. Any known drug therapy for glaucoma may be utilized.

FIGS. 4B-F depict a detailed external view of the microshunt. In some aspect, the proximal section may have a bottom peripheral surface that is perpendicular to the lumen of the microshunt. A receiving thread arrangement may be appropriately located on the peripheral surface. The receiving thread arrangement may be sized and configured to releasably receive a screw thread arrangement for coupling together, wherein the screw thread arrangement may be disposed at the distal end of a fluid delivery element which has a lumen for transporting the infusing fluid into the aqueous cavity for therapeutic purposes. In one embodiment, the coupling of the receiving thread arrangement and the screw thread arrangement effects the fluid infusion through the lumen leak-proof.

In one embodiment, the outlet side openings, each of which may be in fluid communication with the lumen for transmission of aqueous, may be arranged spaced apart around the circumferential periphery of the outlet section.

Figure 5:
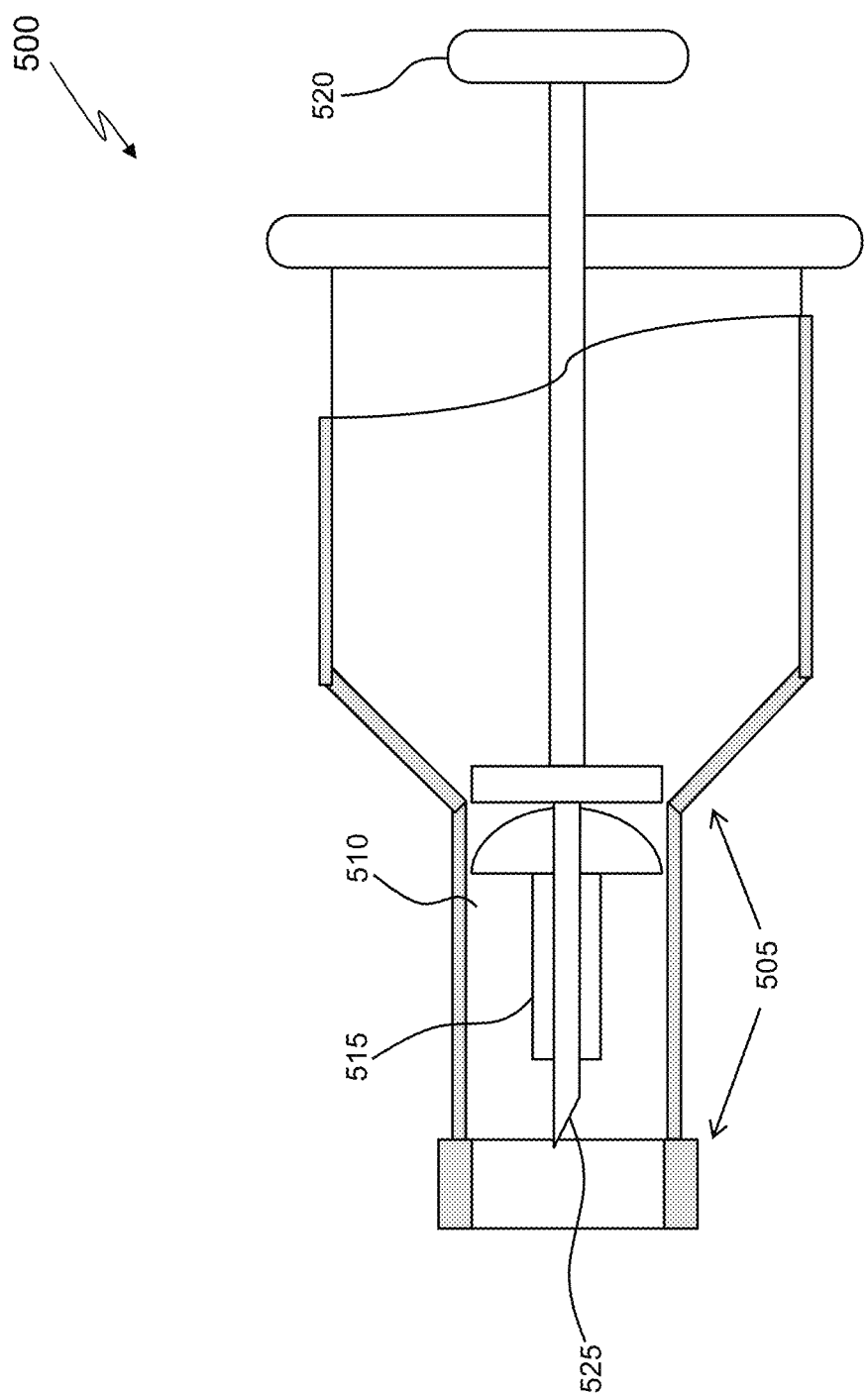
FIG. 5 shows an embodiment of an applicator for delivering a microshunt into the cornea.

FIG. 5 shows an embodiment of an applicator (500) for delivering a microshunt into the cornea, the applicator having a fixture body (505). The distal portion comprises a cutting means (525) sharp enough for creating an incision in and through the cornea for the microshunt (515) placement. The microshunt may be tightly placed within the cannula lumen (510) of the applicator and retained by a plunger-type (520) deployment mechanism. The microshunt is deployed from the applicator once the distal section passes beyond the corneal endothelium and into the anterior chamber. In one aspect, the microshunt deployment may be facilitated by the plunger-type deployment mechanism with an associated deployment actuator mounted on the handle of the applicator. The microshunt may be releasably coupled with a fluid restricting or fluid delivery element at any convenient time during the procedure. In one aspect, the screw-unscrew coupling steps between the microshunt and the fluid delivery element may be carried out by suitably rotating the fluid restricting or fluid delivery element with reference to the microshunt receiving thread arrangement.

In one embodiment, the microshunt device may have a length ranging from about 300 um to over 1000 um. Optionally, the device may have an outside diameter ranging between about 30 µm and about 500 µm, with the lumen having an exemplary set of diameters ranging between about 20 µm and about 250 µm, respectively. In addition, the device may have a plurality of lumens to facilitate transmission of multiple flows of aqueous or infusing fluid.

In a method embodiment for increasing aqueous outflow in the eye of a patient, to reduce intraocular pressure therein, the method may comprise the step of bypassing the trabecular meshwork. While in use, the device may be placed through the cornea, through a slit or opening. This opening may be created by use of a laser, a knife, thermal energy (radiofrequency, ultrasound, and microwave), cryogenic energy, or any other available surgical cutting instrument. The opening may also be horizontal or substantially horizontal, i.e., extending longitudinally in the same direction as the circumference of the limbus (see FIG. 1). Other opening directions may also be used, depending on the set of circumstances. The opening may be oriented at any angle, relative to the circumference of the limbus that is appropriate for inserting the device through the cornea and into the anterior chamber.

Figure 6B:
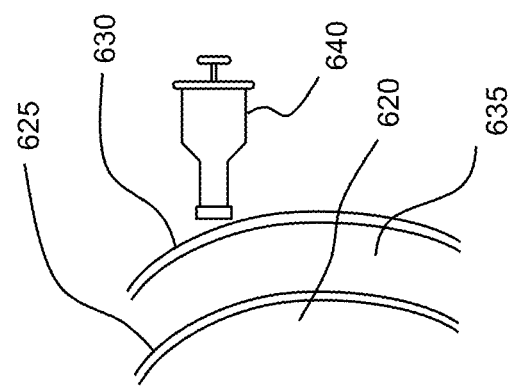
FIG. 6B depicts a side view of a method by which the microshunt is implanted within the cornea.
Figure 6A:
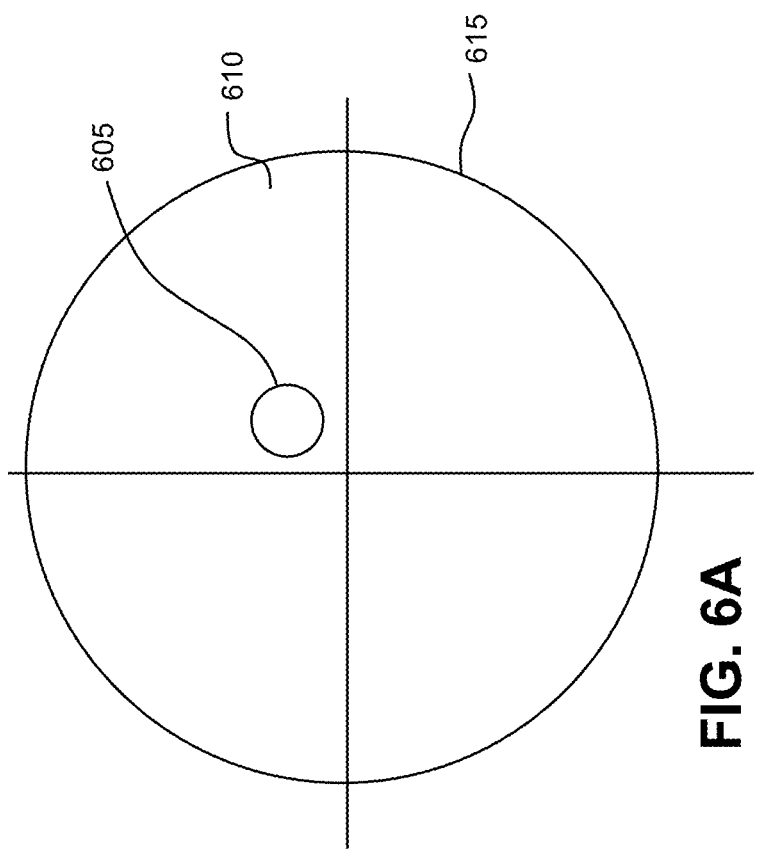
FIG. 6A depicts a front view of a method by which the microshunt is implanted within the cornea.
Figure 6C:
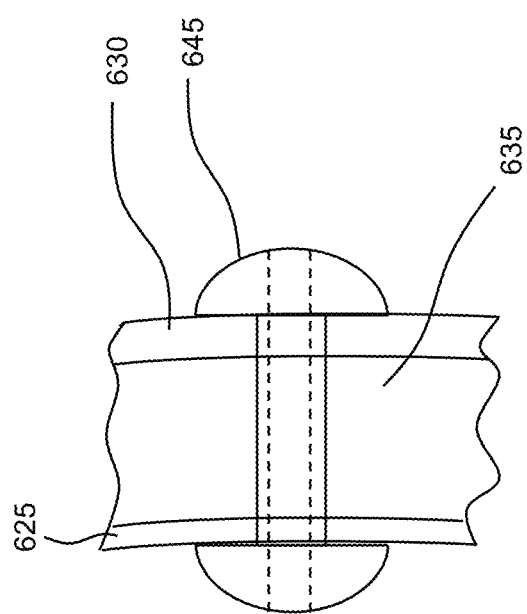
FIG. 6C depicts a side view of a method by which the microshunt is implanted within the cornea.

FIGS. 6A-C generally illustrate a method by which the microshunt (645) may be implanted within the cornea. FIG. 6A depicts a front view and FIGS. 6B and 6C depict a side view. In the illustrated method, a delivery applicator is provided, which preferably comprises a syringe portion and a cannula portion, which may comprise at least one lumen in fluid communication with the aqueous fluid coming from the eye. A holder at the distal portion of the cannula portion for holding the device may comprise a lumen, a sheath, a clamp, tongs, a space, and any other available means for holding the device. In the method illustrated in FIG. 6B, the device may be placed into the lumen of the delivery applicator (640) and then advanced to a desired implantation site within the cornea (605). The delivery applicator may then hold the device securely during delivery and may release it when the practitioner initiates deployment actuator of the applicator. The device may be placed against the epithelial surface of the cornea (630), and inserted through the corneal stroma (635) and endothelium (625) so that the lumen of the microshunt communicates with the aqueous in the anterior chamber (620).

The microshunt device may be retained by the corneal tissue. The microshunt device body may have a geometry that may restrict the microshunt device from moving either into or out of the eye after surgical implantation. Alternately, the microshunt device body may have a roughness, radial ridges, helical ridge or similar feature that causes the microshunt device body to remain fixed under the very slight hydrostatic pressure associated with the glaucomatous condition. The microshunt device may be designed to undergo a geometry change during implanting in order to achieve the retention due to geometry features. The cornea may be surgically cut during implantation and allow the microshunt device geometry to be of a fixed type with the cornea healing to form the desired retention.

In one embodiment of the microshunt corneal surgery, a patient may be placed in an appropriate position, prepped, draped, and appropriately anesthetized. A small incision may then be made through the cornea with a self-trephining applicator. The incision may for example have a surface length less than about 1.0 millimeter in length. Through the corneal incision, the anterior chamber may be accessed, thereby forming a through the cornea for stent placement. After the device is appropriately implanted, the applicator may be withdrawn and the corneal microshunt surgery may be concluded.

In some aspect of the microshunt corneal surgery, a method may be presented where fluid may be injected through the microshunt into the anterior chamber. In one embodiment of the microshunt device a method for using a removable applicator, catheter, cannula, or tubing that is placed ab interno through the microshunt into the anterior chamber of an eye adapted for infusing therapeutic liquid into the aqueous cavity may be used. The fluid may be a salt solution such as Balanced Salt Solution, a viscoelastic, any other suitable viscous or non-viscous liquid, or suitable liquid loaded with drug at a concentration suitable for therapeutic purposes without causing safety concerns. A combination of liquids may also be used. The pressure is raised at an appropriate rate of rise to an appropriate level and for an appropriate length of time, as determined through development studies, to provide for the expansion of the outflow structures and/or a clearing of any blockages within them. The procedure may be augmented with other aids to enhance its effectiveness. These aids may include heat, vibration (sonic or ultrasonic), pulsation of a pressure front, pH, drugs, etc.

In another embodiment, a microshunt delivery device may include a microshunt, an applicator, and a suction stabilizer. In one embodiment, the microshunt may be made, at least partially, of a biodegradable—also including bio-erodible—material admixed with a substance for substance slow-release into ocular tissues. In another embodiment, polymer films may function as substance containing release devices whereby the polymer films may be coupled or secured to the microshunt. The polymer films may be designed to permit the controlled release of the substance at a chosen rate and for a selected duration, which may also be episodic or periodic. Such polymer films may be synthesized such that the substance is bound to the surface or resides within a pore in the film so that the substance is relatively protected from enzymatic attack. The polymer films may also be modified to alter their hydrophilicity, hydrophobicity, and vulnerability to fibrin, cells, and/or platelet adhesion and enzymatic attack. The device may be used for a direct release of pharmaceutical preparations into ocular tissues. As discussed above, the pharmaceuticals may be compounded within the device or form a coating on the device. Any known drug therapy for glaucoma may be utilized.

Since a device coated or loaded with a slow-release substance may have prolonged effects on local tissue surrounding the device, the slow-release delivery may be designed such that an effective amount of substance is released over a desired duration. "Substance," as used herein, may also be defined as any therapeutic or active drug that may stop, mitigate, slow-down or reverse undesired disease processes.

Figure 7A:
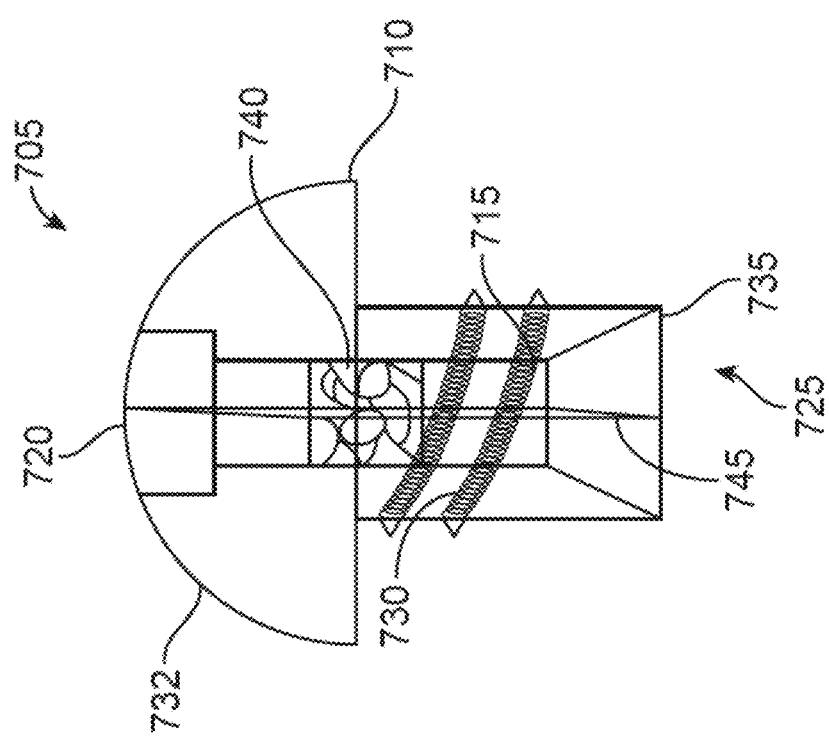
FIG. 7A shows a detailed external view of a microshunt.

FIG. 7A depicts a detailed external view of a microshunt (705) of a microshunt delivery device. In one embodiment, the microshunt (705) may be hollow and may be used in order to facilitate/effect the outflow of aqueous from the anterior chamber through the cornea onto the surface of a cornea (710), and so that the intraocular pressure is reduced. In a cross-section of the illustrated embodiment, the microshunt (705) comprises an inlet section, having an inlet opening (725), a middle section (715), and an outlet section (720) having at least one opening. The middle section (715) may be an extension of, or may be coextensive with, the inlet section. The device comprises at least one lumen within the middle section (715), which is in fluid communication with the inlet opening (725) and the outlet opening (720) thereby facilitating transfer of aqueous through the device.

The lumen and the remaining body of the outlet section may have a cross-sectional shape that is oval, circular, or other appropriate shape. In one embodiment, the middle section may have a length that is roughly slightly larger than the thickness of a normal cornea, which typically ranges between about 400 µm and about 800 µm.

The microshunt (705) allows leakage from the higher pressure environment, e.g., eye interior, to the lower pressure environment, e.g., eye exterior. The microshunt (705) may be made by, for example, molding, thermo-forming, sintering, or other micro-machining techniques. The microshunt may comprise a biocompatible material such that inflammation arising due to irritation between the outer surface of the device and the surrounding tissue is minimized. Biocompatible materials which may be used for the device may include, but are not limited to, titanium, stainless steel, medical grade silicone, e.g., Silastic™, available from Dow Corning Corporation of Midland, Mich.; and polyurethane, e.g., Pellethane™, also available from Dow Corning Corporation. In other embodiments, the device may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicone, polyether ether ketone (PEEK) and/or a mixture of the aforementioned biocompatible materials, and the like. In another embodiment, the microshunt may be made of a biodegradable material selected from a group consisting of poly (lactic acid), polyethylene-vinyl acetate, poly (lactic-co-glycolic acid), poly (D,L-lactide), poly (D,L-lactide-co-trimethylene carbonate), poly (caprolactone), poly (glycolic acid), and copolymer thereof. In other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists, TGF-beta, and other anti-glaucoma drugs, or antibiotics), and similar material.

In one embodiment, the distal end of the microshunt (705) includes a cutting edge (735). In one embodiment, the cutting edge (735) may be similar to the end of a biopsy punch. In one embodiment, the cutting edge (735) may be a sharp edge (e.g., a scalpel-like edge). In the event that a partial-thickness hole in the cornea is created with a biopsy punch (instead of a full-thickness hole), the cutting edge (735) of the microshunt may cut through the remaining corneal layers as the microshunt (705) is pushed or screwed into the corneal hole. If the distal end of the microshunt were not sharp, then the distal end of the microshunt (705) may not be able to penetrate the remaining corneal layers. Additionally, if the distal end of the shunt were not sharp, collapse of the anterior chamber with possible damage to lens and/or iris may result from the force of the distal end of the microshunt (705); however, the sharp cutting edge (735) may minimize force applied to the cornea to prevent the collapse of the anterior chamber and potential damage to lens and/or iris.

In one embodiment, the microshunt (705) may include a helical cutting threading (730) around the periphery of the microshunt (705) for screwing of the microshunt (705) into the cornea. In one embodiment, the helical cutting threading (730) may be sharp to facilitate the screwing of the microshunt (705) into the cornea to aid in insertion/retention of the microshunt (705). Both the helical threading (730) and the distal cutting edge (735) are required if only a partial thickness hole is made in the cornea. If a full-thickness hole is made in the cornea, then only the helical threading (730) may be required.

Figure 7B:
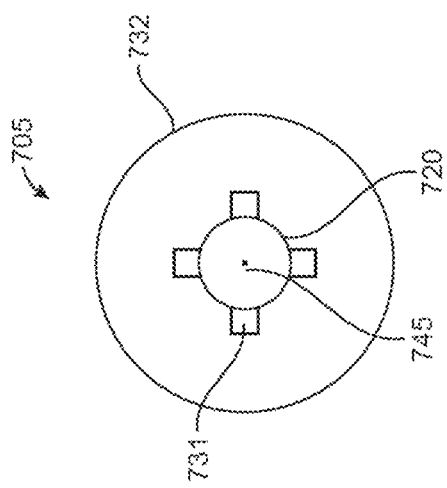
FIG. 7B shows a detailed top elevation view of the microshunt of FIG. 7A.
Figure 8B:
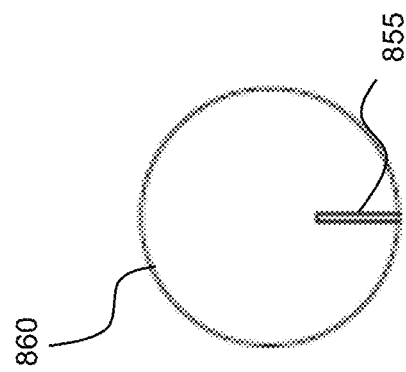
FIG. 8B shows a top plan view of the applicator of FIG. 8A.

The top of the microshunt (705) may have a non-circular, convex head (732) which integrates with the accommodating end of a plunger or screw-type actuator (820) (see FIG. 8). With respect to FIG. 7B, a plurality of slots (731) are disposed around the periphery of the outlet opening (720) of the head (732). In one embodiment, the head (732) has more than 4 slots (731). In one embodiment, the head (732) has less than 4 slots (731). In one embodiment, two of the slots (731) opposite one another around the outlet opening (720) may be sized and configured to releasably receive the plunger or screw-type actuator (832) to the microshunt (705).

With respect to FIG. 7A, the microshunt (705) may further comprise a nanofilter (740), which is tightly retained within a lumen. The nanofilter (740) may be sized and configured for maintaining a safe (normal) intraocular pressure of the fluid within the anterior chamber for a suitable period of time. Alternatively, the nanofilter (740) may be situated in any location within the device such that fluid flow is restricted and intraocular pressure is maintained at a safe level within the anterior chamber. In one embodiment, the nanofilter (740) may be made of a material selected from, but not limited to, the following filter materials: expanded polytetrafluoroethylene, cellulose, ceramic, glass, Nylon, plastic, silicone, and fluorinated material such as polyvinylidene fluoride ("PVDF").

Figure 7C:
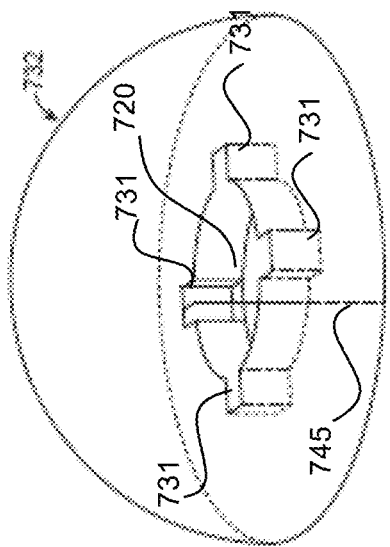
FIG. 7C shows a perspective view of a head of the microshunt of FIG. 7A.

During manufacture of the microshunt assembly, a wire (745) may be used to pull the nanofilter (740) into the lumen of the microshunt (705). After the nanofilter (740) is pulled into the lumen of the microshunt (705), the distal (e.g., anterior chamber) end of the wire (745) may be cut and then bent into a U or V shape, as shown in FIG. 7C. In one embodiment, the distal end of the wire (745) may not contact the lens or iris. Traction may then be applied on the wire (745) to pull the formed U- or V-shaped end of the wire (745) into the microshunt (705). This may prevent the distal end of the wire (745) from contacting the lens or iris in the event of anterior chamber collapse. In one embodiment, the wire (745) is made of silver to provide an antimicrobial effect.

In one embodiment, the proximal (corneal) end of the wire (745) may then also be cut and folded in an angle, for example, a 90 degree angle, such that the proximal end of the wire (745) may fit into at least one of the slots (731) in the head (732) of the microshunt (705). In one embodiment, the proximal end of the wire (745) may not protrude above the level of the head (732) of the microshunt (705) as to avoid ocular pain or irritation when the eyelid closes over the cornea during blinking. The distal U- or V-shaped end and the proximal 90 degree bend prevent the nanofilter (740) from being dislodged from the microshunt (705) into the anterior chamber. In one embodiment, bending the wire (745) at both the proximal and distal ends may prevent unintended migration of the nanofilter (740) out of the microshunt lumen.

The wire (745) may be used at a later time to remove the nanofilter (740) in the event of filter plugging. In such an event, a new nanofilter may be placed in the cornea-implanted microshunt (705). The proximal end of the wire (745) may also be glued in place, such as with an appropriate adhesive mechanism. In one embodiment, the adhesive mechanism may be glue, such as cyanoacrylate glue or silicone glue. The glue may prevent movement of the nanofilter (740). In another embodiment, the corneal end of the wire (745) may not be bent over 90 degrees, and a hollow center in a portion of a flow delivery element accommodates the wire, as described in further detail below.

Figure 8A:
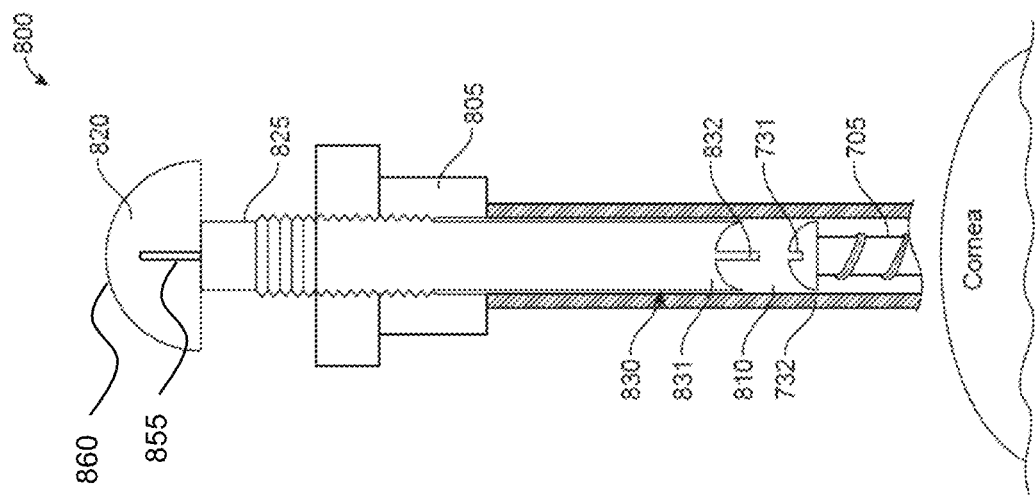
FIG. 8A shows an embodiment of an applicator for delivering the microshunt of FIG. 7A into the cornea.

FIG. 8A shows an embodiment of a delivery device (800) for delivering the microshunt (705) into the cornea, the delivery device (800) having a fixture body (805). The microshunt (705) may be tightly placed within the cannula lumen (810) of the applicator (800) and retained by the screw-type actuator (820). In one aspect, the microshunt deployment may be facilitated by the screw-type actuator (820) with an associated deployment actuator mounted on the handle of the delivery device (800).

Figure 9:
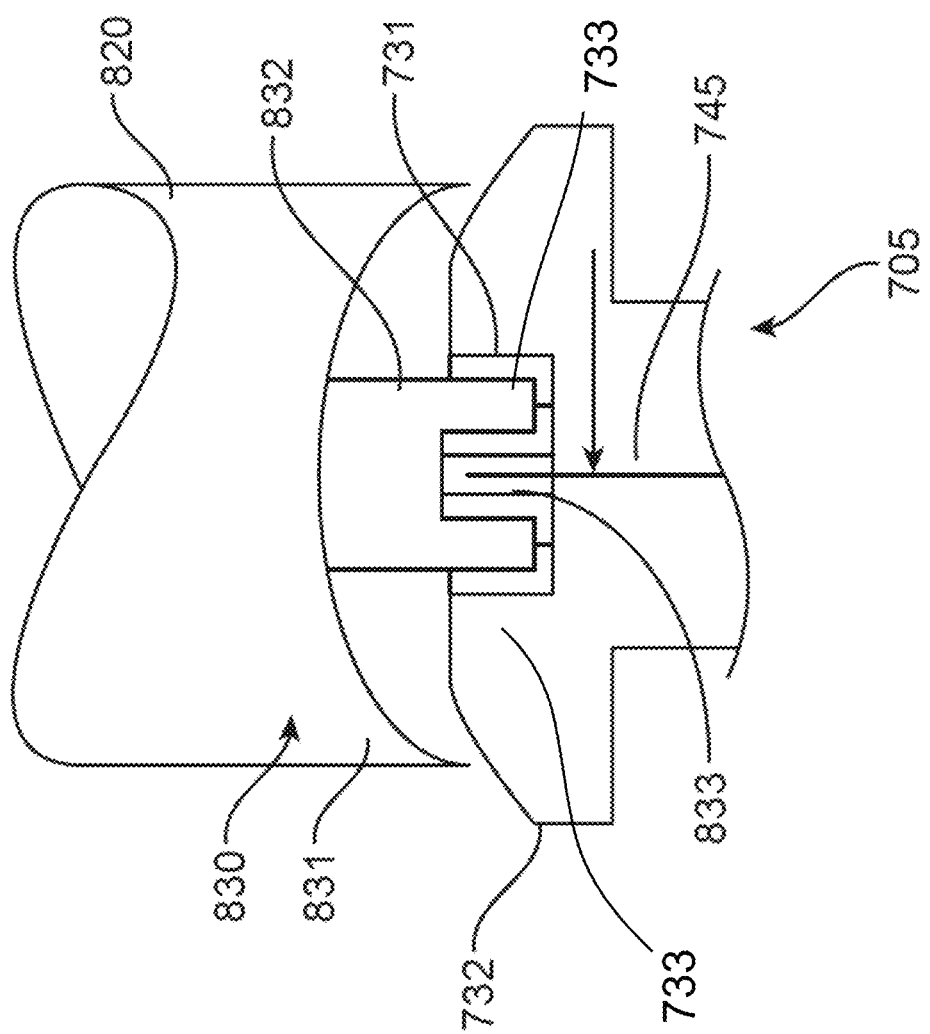
FIG. 9 shows an enhanced view of a connection between a fluid delivery element and the microshunt of FIG. 7A.

In one embodiment, the actuator (820) may include a helical shaft (825) and a microshunt coupling arrangement (830) at the distal end of the screw-type actuator (820). A microshunt coupling arrangement (830) may provide for releasably coupling the screw-type actuator (820) with the microshunt (705). More specifically, and also with reference to FIG. 9, the microshunt coupling arrangement (830) may have a concave end portion (831) and rib (832). In one embodiment, the rib (832) fits into the slots (731) of the microshunt (705), and the concave end portion (831) is curved to accommodate the convex shape of the head (732) of the microshunt (705). In one embodiment, the proximal end of the wire (745) is fit into one of the remaining slots (731) not being used to fit the rib (832). As described above, the microshunt coupling arrangement (830) may further include a gap (833) in a portion of the rib (832) of the screw-type actuator (820) which accommodates the wire (745). In one embodiment, the helical cutting threads (730) of the microshunt (705) and helical shaft (825) are oriented in the same direction (either both clockwise or both counterclockwise). In one embodiment, the length of travel of the microshunt (705) as the microshunt is rotated into the cornea is equal to the length of travel of the screw-type actuator (820) as the screw-type actuator (820) is depressed or turned.

The microshunt (705) may be coupled or decoupled to the microshunt coupling arrangement (830) at any convenient time during the procedure. In one aspect, the screw-unscrew coupling steps between the microshunt and the screw-type actuator (820) may be carried out by suitably rotating the screw-type actuator (820). With respect to FIGS. 8A and 8B, the microshunt (705) may be delivered into the cornea by twisting a knob (860) at the end of the screw-type actuator (820). The knob (860) may be turned (or pushed) to screw the microshunt (705) into the cornea. In one embodiment, the knob (860) may have indicator marks (855) to show how far to turn the knob (860) to insert the microshunt (705) into the cornea.

In one embodiment, the delivery device (800) may have a length ranging from about 10 mm to over 20 mm. In one embodiment, the inside diameter of the delivery device lumen (810) may match (or may be slightly larger than) the outer diameter of the microshunt (705) so that the microshunt (705) fits snugly into the lumen of the delivery device (800). In one embodiment, the outer diameter of the delivery device (800) may be two or more times the inner diameter of the lumen to provide for rigidity of the delivery device (800). In one embodiment, the fixture body (805) may be approximately in the range of 3-6 mm.

Figure 10:
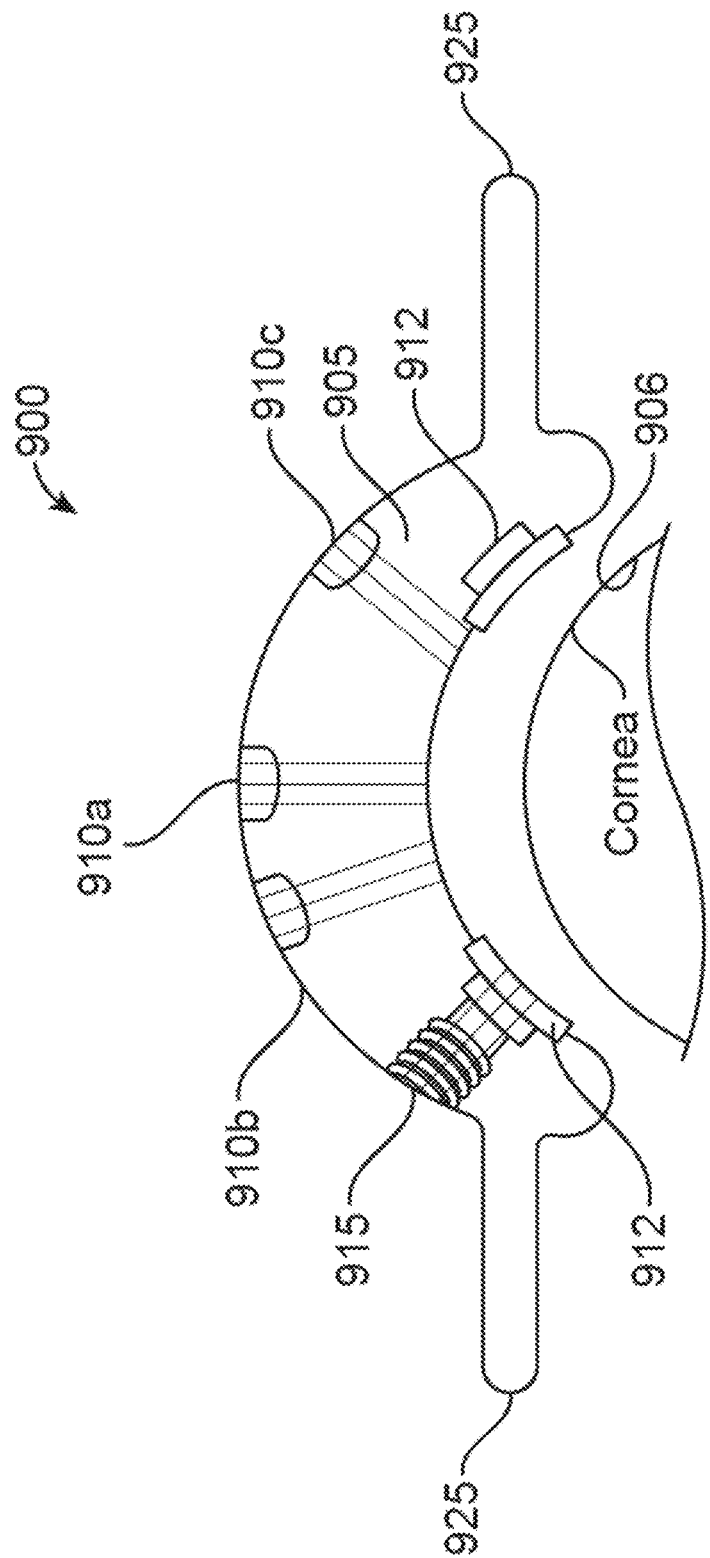
FIG. 10 shows a detailed external view of a suction stabilizer.
Figure 11:
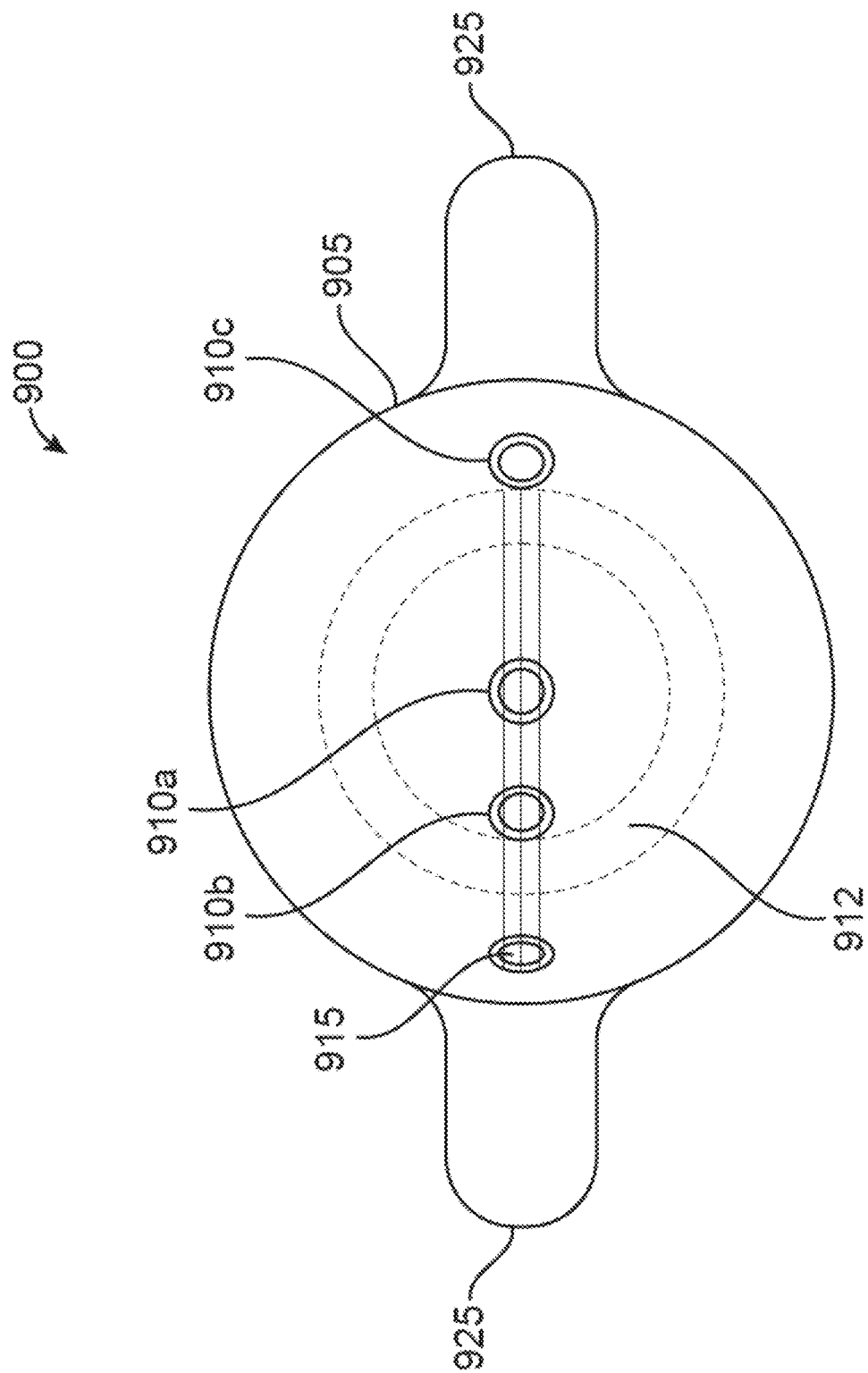
FIG. 11 shows a detailed top elevation view of the suction stabilizer of FIG. 10.

With respect to FIGS. 10 and 11, a suction stabilizer (900) of the microshunt delivery device is shown. In one embodiment, for an inflated normotensive or hypertensive globe, a partial (e.g., ¾, ⅘, etc.) or full thickness circular hole may be created in the central, paracentral, or lateral portion of a cornea (906). In one embodiment, the hole may have a restricted depth by using a biopsy punch to create a corneal hole. In one embodiment, the biopsy punch has restricted depth of 0.6 mm to 0.7 mm. In one embodiment, the partial-thickness corneal hole may have a restricted depth, using a restricted-depth biopsy punch to create a corneal hole. The suction stabilizer (900) may include a body (905) with three holes (910) located on an upper, convex side of the body (905). In one embodiment, the holes (910) may include a central hole (910a), paracentral hole (910b), or lateral hole (910c).

The suction stabilizer (900) may be placed on the cornea (906) and the hole (e.g., 910a, 910b, or 910c) in the stabilizer may be aligned directly over the hole in the cornea to align the suction stabilizer (900) over the hole created in the cornea to prepare for microshunt insertion. In one embodiment, a partial vacuum may be created when a vacuum device (915), such as a spring-based syringe or the like is attached to a tube (or other attachment port) inserted in a suctioning hole (913). In one embodiment, the suction stabilizer (900) may have a suctioning ring (912) (described in further detail below), such that the cornea is sucked onto the concave bottom side of the stabilizer (900). Suction is maintained with a stopcock or with the spring-loaded syringe.

The vacuum suction may provide rigidity to the cornea for insertion of the microshunt (705), preventing anterior chamber collapse, and therefore keeping the microshunt (705) away from the lens and/or iris during insertion of the microshunt (705).

The applicator (800) having the microshunt (705) coupled to the screw-type actuator (820) may be inserted into the appropriate hole in the vacuum stabilizer. For example, if a paracentral hole is made in the cornea, then the delivery device (800) may be inserted into the aligned paracentral hole (910b) of the stabilizer (900). The screw-type actuator (820) may then be turned or depressed to screw the microshunt (705) into the hole in the cornea. In one embodiment, the screw-type actuator (820) may be removed from the stabilizer (900), and the vacuum seal is then broken by releasing the spring-loaded syringe (or opening the stopcock). The stabilizer (900) may then be removed from the cornea, leaving the microshunt (705) in the cornea.

In one embodiment, a pair of side flanges (925) may stabilize the suction stabilizer (900) on the orbital bones around the globe, such that when the cornea (906) is suctioned onto the suction stabilizer (900), the stabilizer (900) maintains the globe elevated above or at the level of the orbital bones; therefore, preventing the cornea from collapsing onto the surface of the lens and/or iris when the pressure is placed on the cornea when inserting the microshunt (705) through the corneal hole. In one embodiment, the side flanges (925) may be detachable from the suction stabilizer (900) in order to suit a particular surgical situation. In another embodiment, the side flanges (925) may be fixed to the body (905).

In one embodiment, a separate anterior fluid delivery system, such as an anterior chamber maintainer or infusing a viscoelastic substance into the anterior chamber, may also be used to maintain the anterior chamber volume and/or prevent collapse during microshunt implantation.

In one embodiment, the holes 910a,b,c in the suction stabilizer (900) may be drilled such that the hole in the suction stabilizer is perpendicular to the corneal surface when the cornea becomes suctioned to the suction stabilizer.

In one embodiment, the suction stabilizer body (905) may be made from a clear rigid or semi-rigid material (e.g., resin) that may be autoclavable or may be sterilized by another method, such as with a chemical solution, ethylene oxide gas, etc. The clear material provides for visualization of the cornea and distal portion of cornea while implanting the microshunt to see if the microshunt (705) is in the anterior chamber. The curved shape of the stabilizer body (905) may also provide for magnification of the cornea and distal portion of the cornea. In one embodiment, the magnification may further provide for viewing of intraocular structures. In another embodiment, the magnification may eliminate internal reflection of the cornea. In one embodiment, the underside of the suction stabilizer (900) of which the cornea is sucked onto may be made of a soft flexible material, such as a silicone flange, which promotes or enhances suction of the cornea (906) onto the suction stabilizer (900). In one embodiment, the soft flexible material allows for warping and flexing to accommodate any unevenness on the surface of the cornea and/or variations from one cornea to another, since each eye may have a slightly different shape and size, as well as differences between species and among different ages, races (among humans) and breeds within a species. In one embodiment, the flexible material may further provide for protecting the cornea as well as the suction stabilizer (900) from scratches. Additionally, the flexible material, e.g., silicone, may also be sterilized.

In one embodiment, the side flanges (925) may be made of a semi-rigid material, such as the same material as the body (905) or of a rigid material, such as plastic to prevent the suction stabilizer (900) and cornea (906) from being pushed into the orbit when placing pressure on the cornea during insertion of the microshunt (705). Once the suction stabilizer (900) and hole (910) associated with the suction stabilizer (900) are in place over the corresponding corneal hole, the vacuum device (915) may be deployed and the cornea (906) may be sucked onto the suction stabilizer (900).

Figure 12:
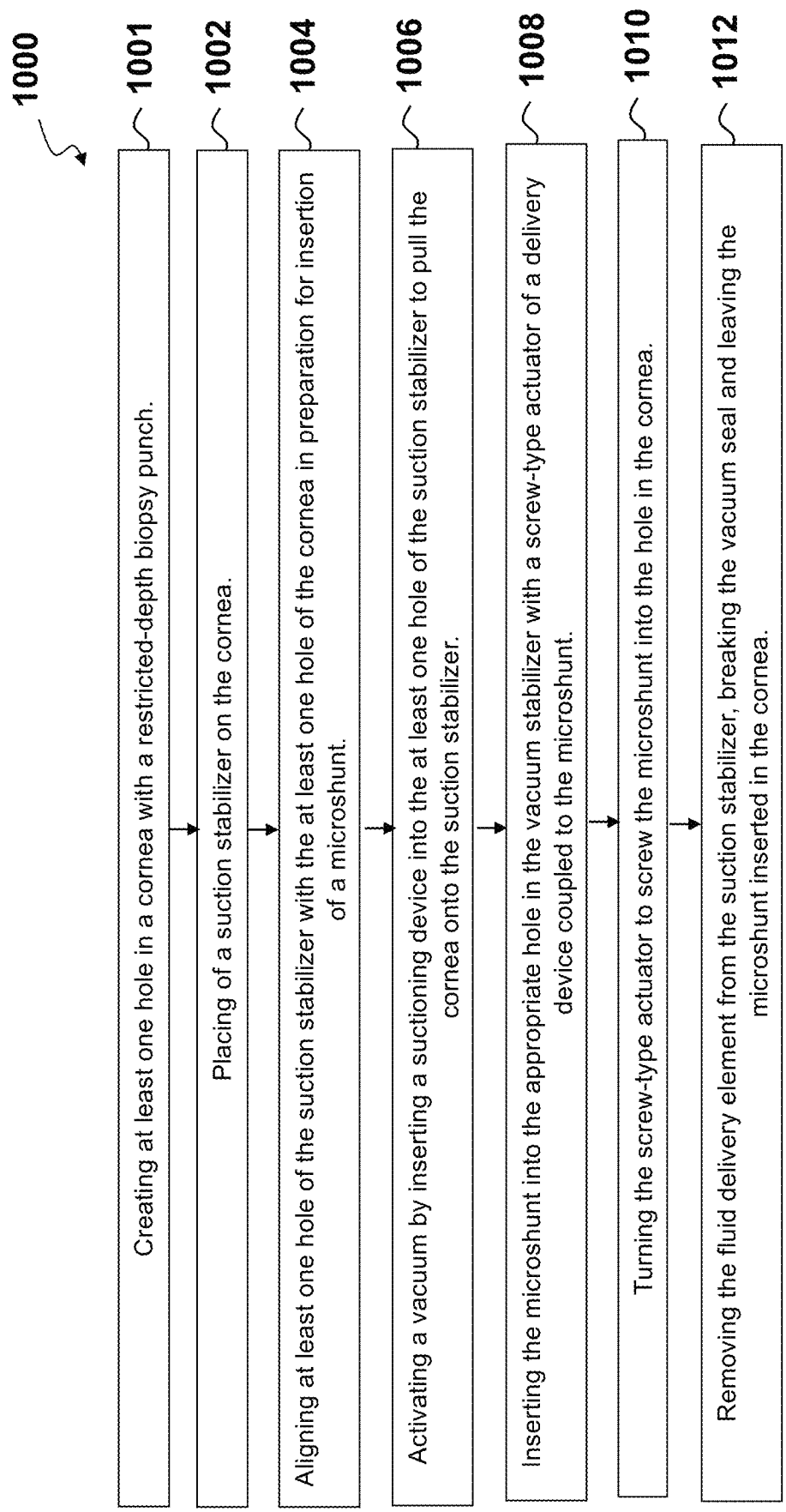
FIG. 12 shows a flowchart for a method for delivering a microshunt into the cornea.

With respect to FIG. 12, a method (1000) for delivery of a microshunt is illustrated. At step (1001), at least one hole in a cornea is created with a restricted-depth biopsy punch. In one embodiment, the restricted-depth biopsy punch is a full-thickness biopsy punch. In another embodiment, the restricted-depth biopsy punch is a partial-thickness biopsy punch. In one embodiment, the biopsy punch has restricted depth of 0.6 mm to 0.7 mm. In one embodiment, at least one partial-thickness hole is created instead of a full-thickness hole. At step (1002), a suction stabilizer may be placed on a cornea. At step (1004), at least one hole in the stabilizer may be placed directly over a hole in the cornea to align the suction stabilizer over the hole created in the cornea to prepare for microshunt insertion. At step (1006), a suctioning device may be inserted in the stabilizer, and a vacuum may be activated such that the cornea may be sucked onto a concave bottom side of the stabilizer. In one embodiment, the vacuum may be created by access of the suctioning device, e.g., a spring-loaded syringe, through an annular suctioning hole. In some embodiments, the stabilizer may have more than one suctioning hole. The vacuum suction may provide rigidity to the cornea for insertion of the microshunt, preventing anterior chamber collapse, and therefore keeping the microshunt away from the lens and/or iris during insertion of the microshunt.

In additional embodiments, a pair of side flanges may stabilize the suction stabilizer on the orbital bones around the globe, such that when the cornea is suctioned onto the suction stabilizer, the suctioning ring maintains the globe elevated above or at the level of the orbital bones; therefore, preventing the cornea from collapsing onto the surface of the lens and/or iris when the pressure is placed on the cornea during the inserting of the microshunt through the corneal hole. In one embodiment, the side flanges are detachable from the suction stabilizer in order to suit a particular surgical situation. In another embodiment, the side flanges are fixed to the body.

At step (1008), a delivery device may insert the microshunt into the appropriate hole in the vacuum stabilizer with a screw-type actuator coupled to the microshunt. For example, if a paracentral hole is made in the cornea, then the microshunt may be inserted into the aligned paracentral hole of the stabilizer. At step (1010), the screw-type actuator may then be turned (or depressed) to screw the microshunt into the hole in the cornea, such that fluid now passes from the anterior chamber, through the microshunt, and onto the corneal surface.

At step (1012), the screw-type actuator may be removed from the stabilizer, and the vacuum seal is broken. The stabilizer may then be removed from the cornea, leaving the microshunt in the cornea.

In one embodiment, a separate anterior chamber maintainer may also be used to maintain the anterior chamber volume/prevent collapse during shunt implantation. In another embodiment, a viscoelastic substance may be injected into the anterior chamber. In one embodiment, the viscoelastic substance may be evacuated from the anterior chamber after the microshunt is implanted.

In one embodiment, the suction stabilizer body may be made from a clear rigid or semi-rigid material (e.g., resin) that may be autoclavable or may be sterilized by another method, such as with a chemical solution, ethylene oxide gas, etc. The clear material provides for visualization of the cornea and distal portion of cornea while implanting the shunt to see if the microshunt is in the anterior chamber. The curved shape of the stabilizer body may also provide for magnification of the cornea and distal portion of the cornea.

In one embodiment, the underside of the suction stabilizer of which the cornea is sucked onto may be made of a soft flexible material, such as a silicone flange, which promotes or enhances suction of the cornea onto the suction stabilizer. In one embodiment, the soft flexible material allows for warping and flexing to accommodate any unevenness on the surface of the cornea and/or variations from one cornea to another, since each eye may have a slightly different shape and size, as well as differences between species and among different ages, races (for humans) and breeds within a species.

In one embodiment, the side flanges may be made of a rigid material to prevent the suction stabilizer and cornea from being pushed into the orbit when placing pressure on the cornea during insertion of the microshunt. Once the suction stabilizer and its associated hole are in place over the corresponding corneal hole, the vacuum may be deployed and the cornea (906) is sucked onto the suction stabilizer.

The disclosed embodiments of the microshunt device may provide a method to simplify microshunt corneal surgeries. Accordingly, the surgery may potentially be performed on an outpatient basis under topical or local anesthesia, or with a brief general anesthesia, with improved prognosis for retaining vision, greatly reduced morbidity and expense. The method and device may be used for short-term or long-term control of glaucoma in all species of animals, especially, dogs, cats, and horses, including humans.

It is contemplated that various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further it is intended that the scope of the present invention herein disclosed by way of examples should not be limited by the particular disclosed embodiments described above

What is claimed is:

1. A microshunt delivery system comprising:
   a microshunt comprising:
   an inlet section comprising at least one lumen and at least one inlet opening;
   an outlet section comprising at least one lumen that connects to at least one outlet opening;
   a head with at least one slot;
   a helical cutting threading around the periphery of the microshunt;

a nanofilter;
a wire;
an actuator comprising:
  a helical shaft;
  a knob;
  a coupling arrangement comprising a concave end portion, the concave end portion including a rib with a gap for insertion into the at least one slot of the head of the microshunt;
a suction stabilizer comprising:
  a body having a plurality of implantation holes;
  at least one suctioning hole;
  a suctioning ring;
wherein at least one implantation hole of the plurality of implantation holes is configured to be aligned with a hole in a cornea;
wherein a vacuum device is configured to be inserted into the at least one suctioning hole, suctioning the cornea to a concave underside of the suction stabilizer; and
wherein the head of the microshunt is configured to couple to the actuator, and the knob is configured to turn to move the microshunt through one of the plurality of implantation holes configured to screw the microshunt into the hole in the cornea.

2. The system of claim 1 wherein the microshunt couples to the actuator via a screw-type actuator.

3. The system of claim 2 wherein the screw-type actuator is configured to turn to screw the microshunt into a hole in the cornea.

4. The system of claim 3 wherein the screw-type actuator is configured to be removed from the stabilizer.

5. The system of claim 3 wherein the stabilizer is configured to be removed from the cornea, leaving the microshunt in the cornea.

6. The system of claim 1 wherein the nanofilter is retained within the at least one lumen.

7. The system of claim 1 wherein the wire is configured to pull the nanofilter into the lumen.

8. The system of claim 1 wherein the at least one suctioning hole is located on an upper, convex side of the suction stabilizer body.

9. The system of claim 1 wherein the at least one implantation hole of the plurality of implantation holes includes at least one of: a central hole, a paracentral hole, and lateral hole.

10. A method of delivering a microshunt into a cornea, the method comprising:
  creating at least one hole in a cornea with a restricted-depth biopsy punch;
  placing of a suction stabilizer on the cornea;
  aligning at least one hole of the suction stabilizer directly over the at least one hole in the cornea to prepare for microshunt insertion;
  activating a vacuum by inserting a suctioning device into the at least one hole of the suction stabilizer to pull the cornea onto the suction stabilizer;
  inserting the microshunt into the aligned at least one hole in the suction stabilizer with a screw-type actuator of a delivery device coupled to the microshunt;
  turning the screw-type actuator to screw the microshunt into the hole in the cornea; and
  removing the screw-type actuator from the suction stabilizer, breaking the vacuum seal and leaving the microshunt inserted in the cornea.

11. A suction stabilizer apparatus comprising:
a body having a plurality of implantation holes;
at least one suctioning hole;
a suctioning ring;
wherein at least one of the plurality of implantation holes is configured to be aligned with a hole in a cornea and to prepare for microshunt insertion;
wherein a vacuum device is configured to be inserted into the at least one suctioning hole, wherein the vacuum device is configured to suction the cornea to a concave underside of the suction stabilizer; and
wherein a head of the microshunt has at least one slot coupled to an actuator.

12. The suction stabilizer apparatus of claim 11 further comprising a plurality of side flanges, wherein the plurality of side flanges are configured to stabilize the suction stabilizer on orbital bones around a globe of the eye.

13. The suction stabilizer apparatus of claim 12 wherein the suction stabilizer apparatus is configured to maintain the globe at a specified level in relation to the orbital bones.

14. The suction stabilizer apparatus of claim 13 wherein the suction stabilizer apparatus is configured to prevent the cornea from collapsing onto the surface of the lens when pressure is placed on the cornea while inserting the microshunt through the corneal hole.

15. The suction stabilizer apparatus of claim 12 wherein the plurality of side flanges are detachable from the suction stabilizer apparatus.

* * * * *